(12) United States Patent
Liversidge

(10) Patent No.: US 9,028,452 B2
(45) Date of Patent: May 12, 2015

(54) SAFETY NEEDLE PACK

(76) Inventor: Barry Peter Liversidge, Colchester (GB)

( * ) Notice: Subject to any disclaimer, the term of this patent is extended or adjusted under 35 U.S.C. 154(b) by 824 days.

(21) Appl. No.: 12/445,119

(22) PCT Filed: Oct. 11, 2007

(86) PCT No.: PCT/GB2007/050622
§ 371 (c)(1),
(2), (4) Date: Apr. 10, 2009

(87) PCT Pub. No.: WO2008/044067
PCT Pub. Date: Apr. 17, 2008

(65) Prior Publication Data
US 2010/0016803 A1  Jan. 21, 2010

(30) Foreign Application Priority Data

Oct. 11, 2006  (GB) .................................. 0620117.2

(51) Int. Cl.
*A61M 5/32* (2006.01)
*A61M 5/00* (2006.01)
*A61M 5/34* (2006.01)
*A61M 5/50* (2006.01)

(52) U.S. Cl.
CPC ............... *A61M 5/326* (2013.01); *A61M 5/002* (2013.01); *A61M 5/347* (2013.01); *A61M 5/5086* (2013.01); *A61M 2005/3247* (2013.01); *A61M 2005/3267* (2013.01); *A61M 2005/3268* (2013.01)

(58) Field of Classification Search
USPC .................. 604/110, 192–198, 241
See application file for complete search history.

(56) References Cited

U.S. PATENT DOCUMENTS 4,961,730 A * 10/1990 Poncy ........................... 604/198
2003/0236502 A1  12/2003 De La Serna et al.

FOREIGN PATENT DOCUMENTS

| EP | 1535640 | 6/2005 |
|----|---------|--------|
| WO | 03/045480 | 6/2003 |
| WO | 2004/071560 | 8/2004 |
| WO | 2006/072807 | 7/2006 |
| WO | WO 2006/082350 | 8/2006 |

OTHER PUBLICATIONS

PCT International Search Report, European Patent Office, PCT/GB2007/050622, Dec. 4, 2007.

* cited by examiner

*Primary Examiner* — Kami A Bosworth
*Assistant Examiner* — Imani Hayman
(74) *Attorney, Agent, or Firm* — Mintz Levin Cohn Ferris Glovsky and Popeo, P.C.

(57) ABSTRACT

A safety needle pack has a safe needle device contained within a housing 10, for use with a syringe 20. The device has a needle hub 16 supporting a needle 17 and a sleeve 22 is slidably mounted on the hub for movement between an initial position to an intermediate position where the tip region 31 of the needle 17 projects from the sleeve 22 and a protecting position. Following use of the safe needle device, the sleeve 22 is moved under the action of a spring 24,29,30 to the protecting position, a locking mechanism 29,40 then restraining the sleeve in that position. The rotational connection of a syringe 20 to the needle hub 16 turns the safe needle device within its housing 10, this causing the sleeve 22 to move rearwardly with respect to the housing from its initial position to its intermediate position so as to be ready for performing a medical procedure.

24 Claims, 8 Drawing Sheets

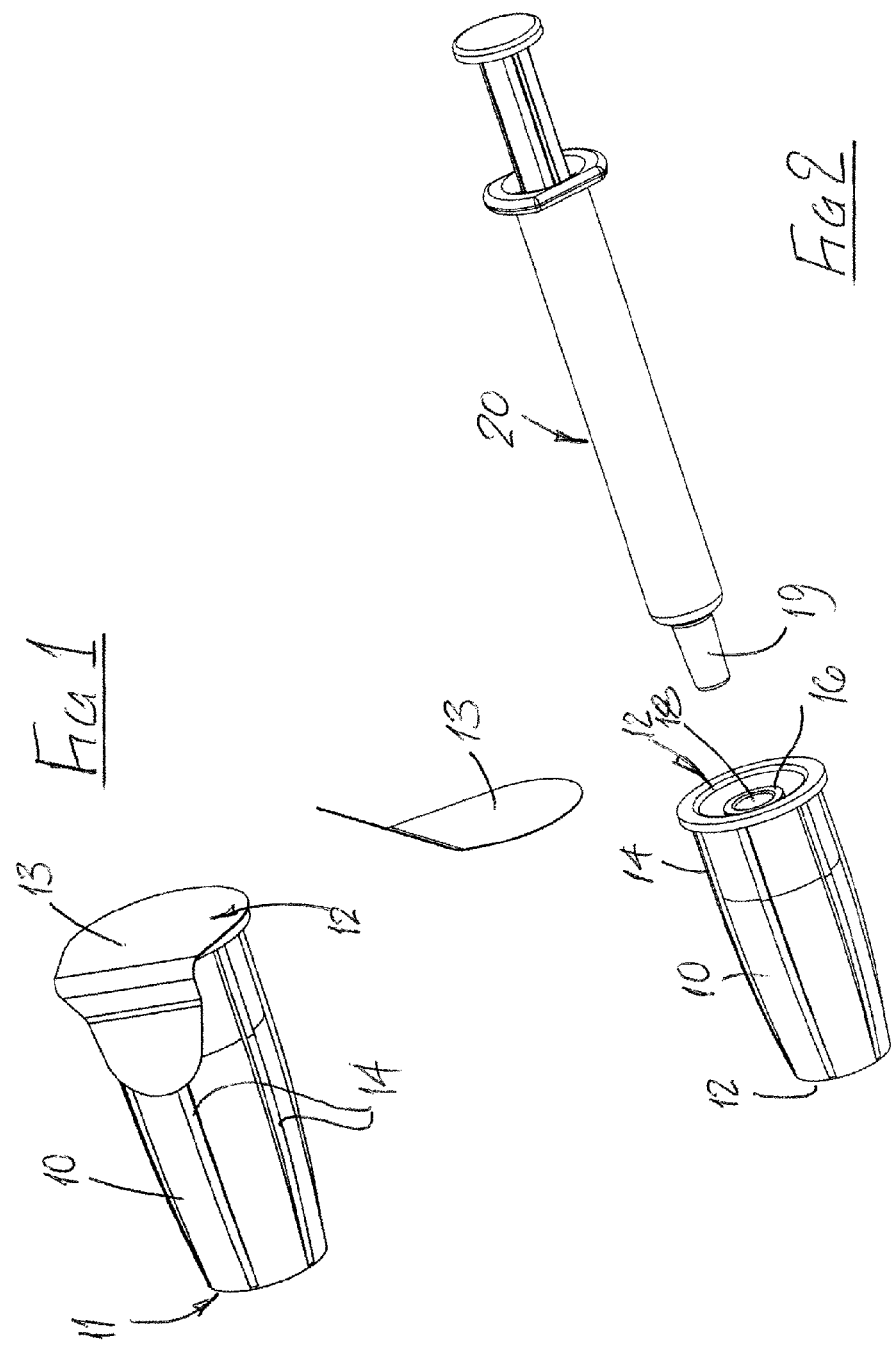

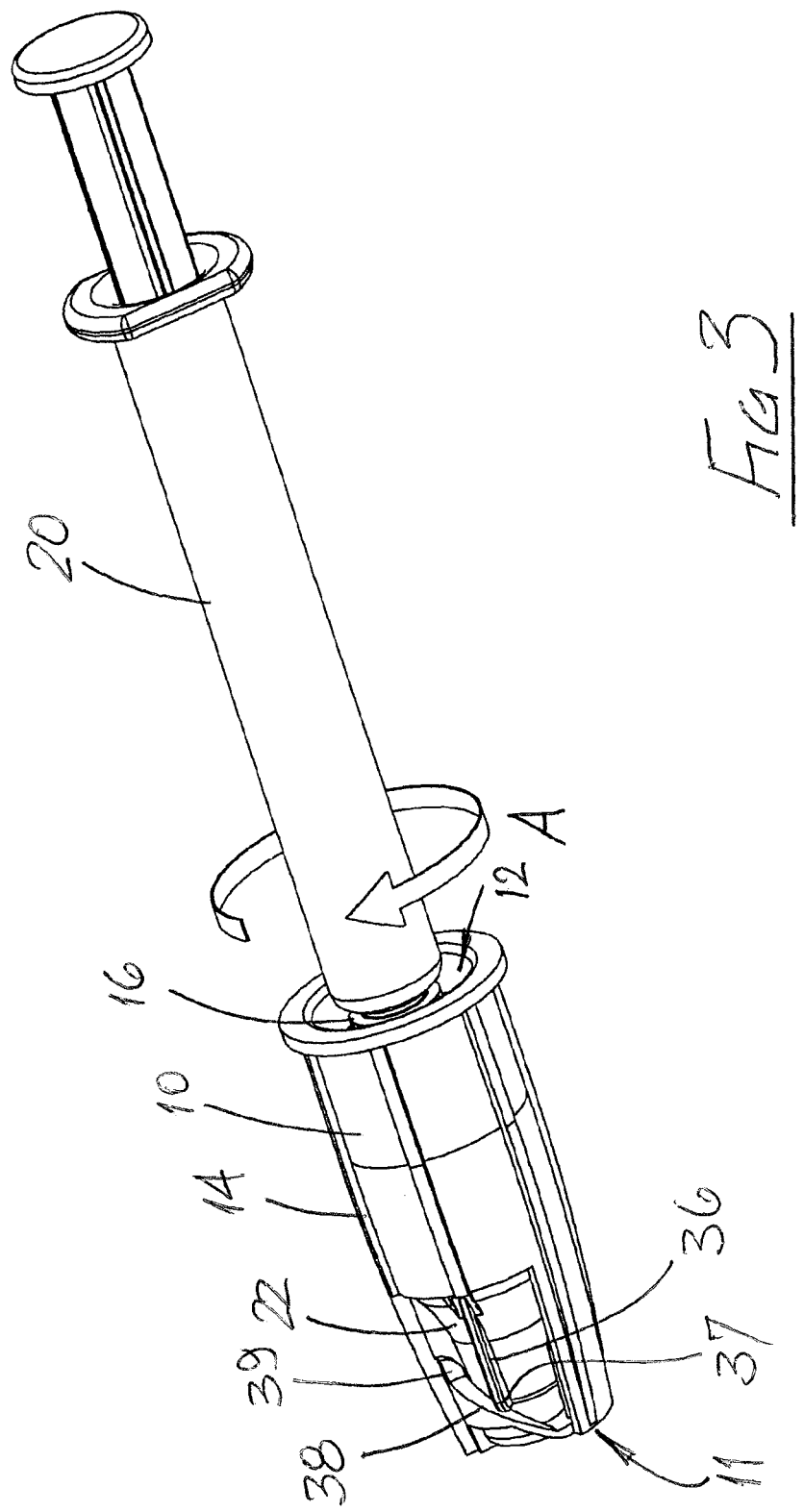

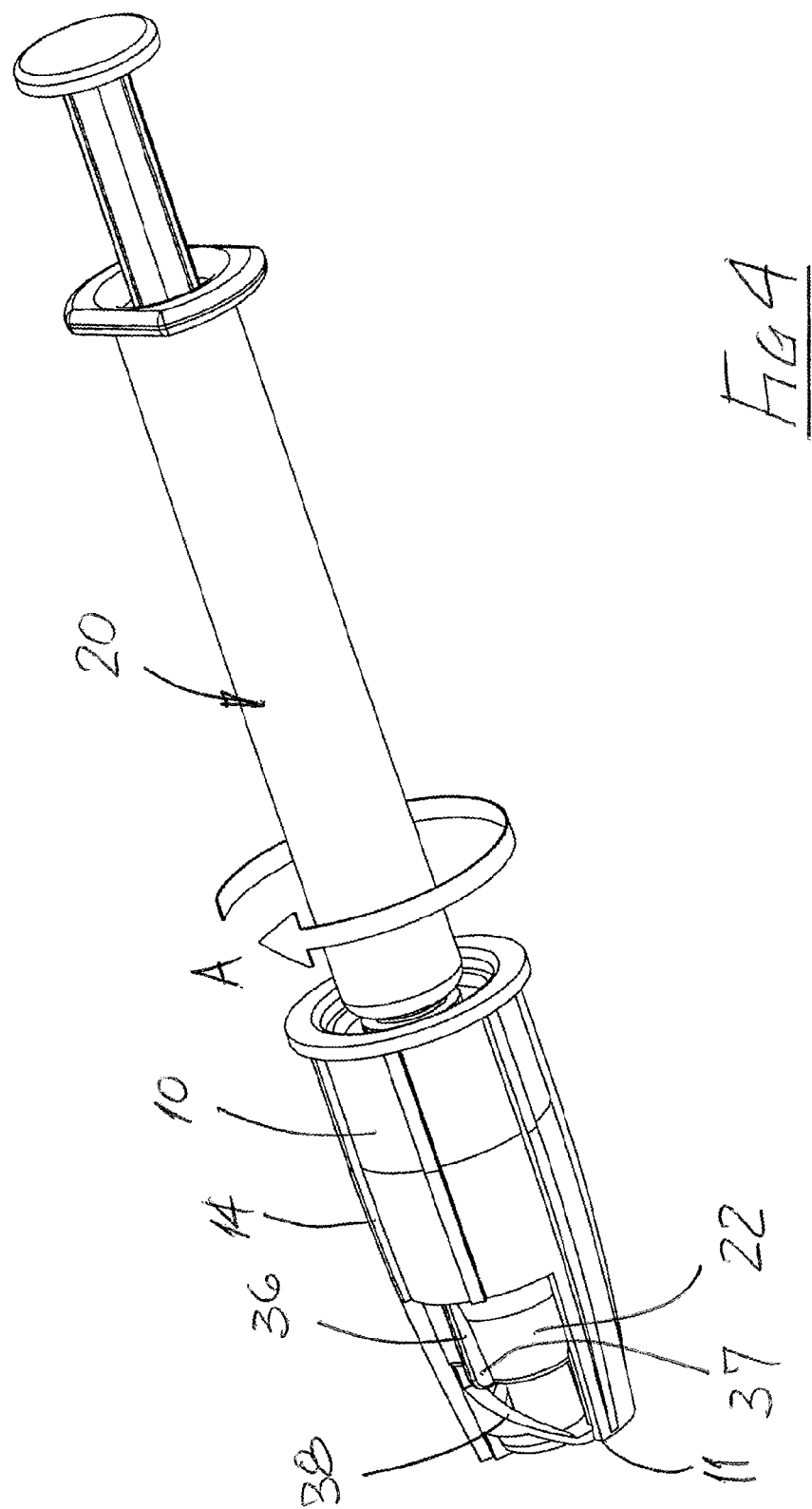

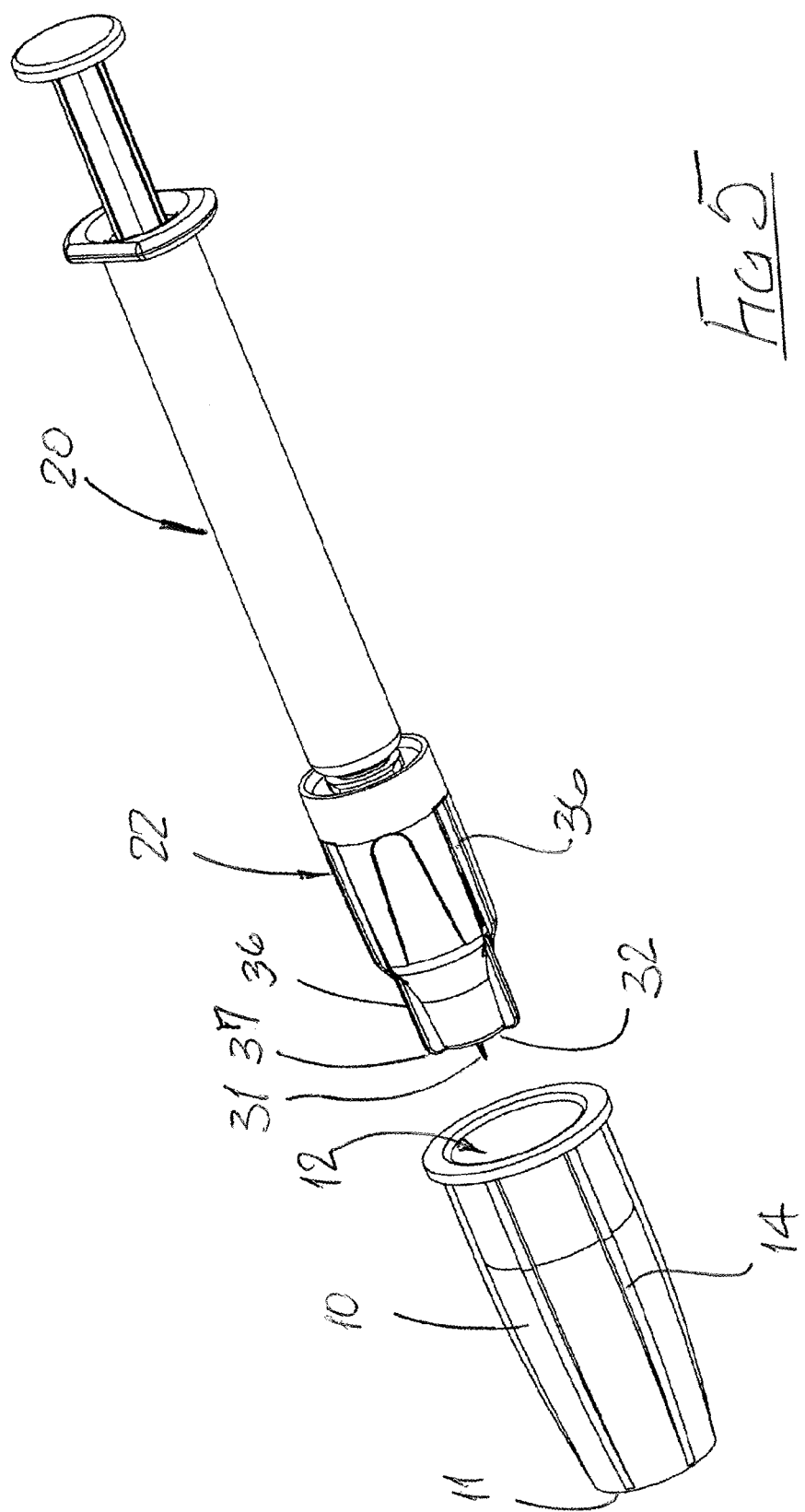

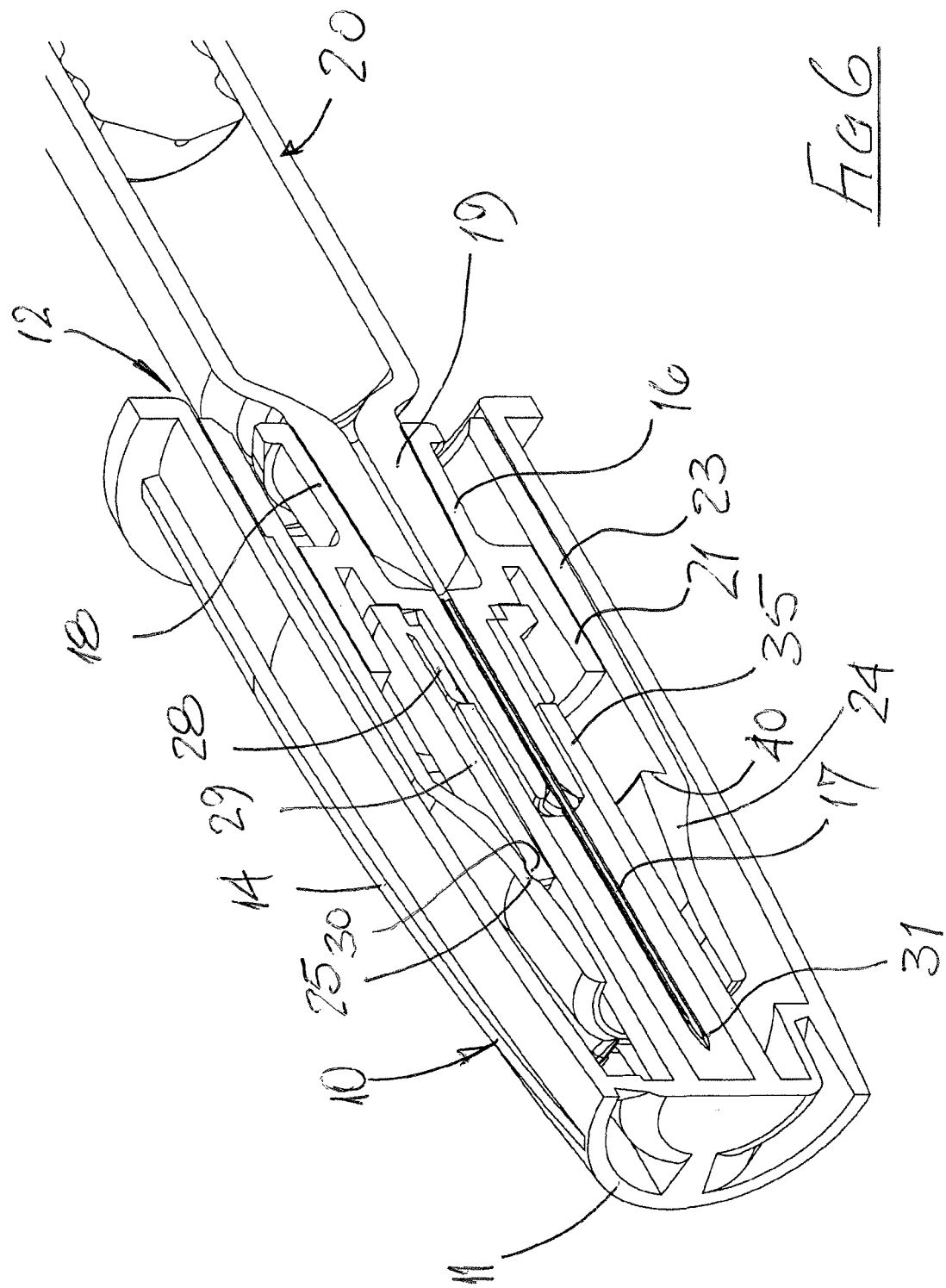

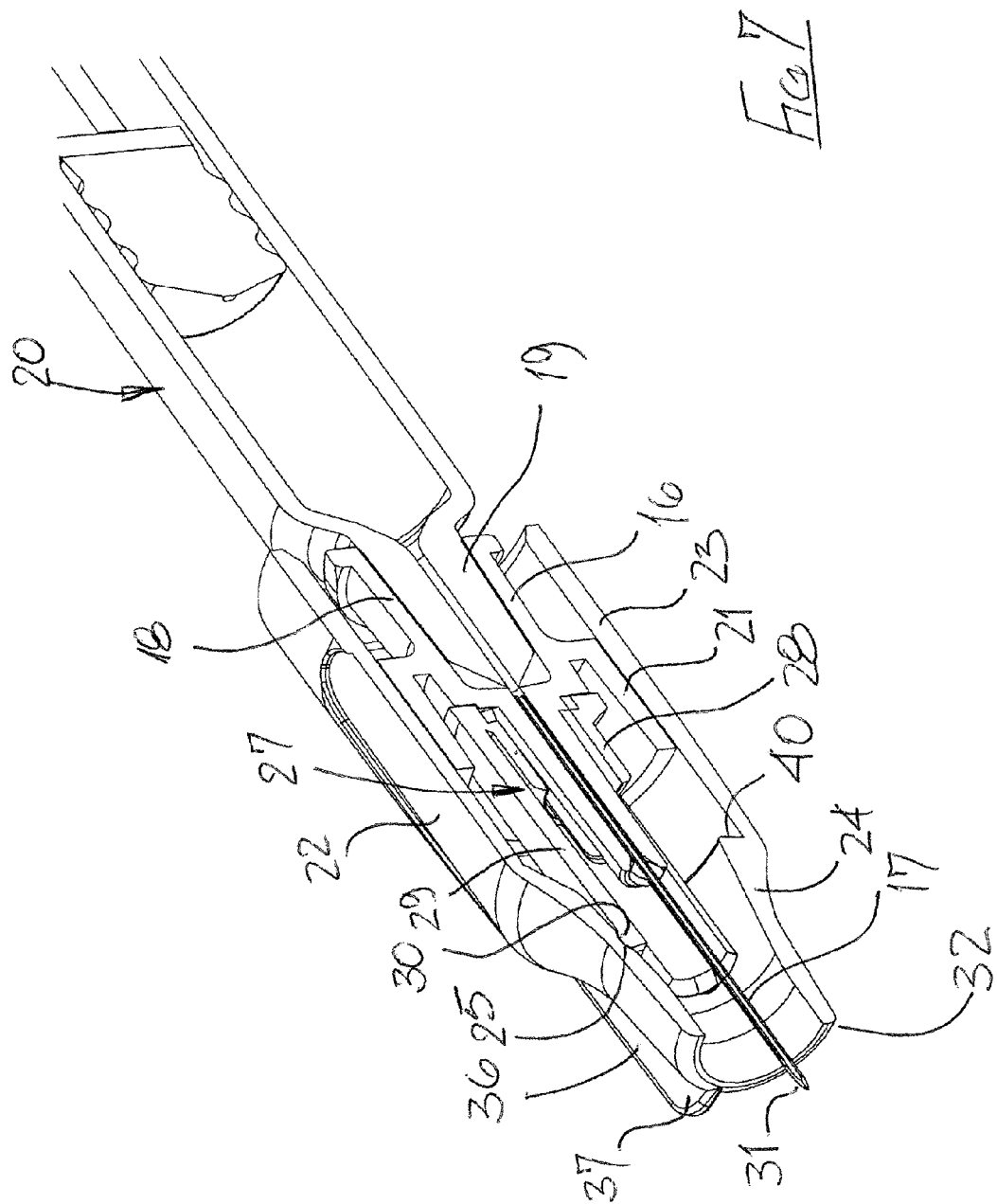

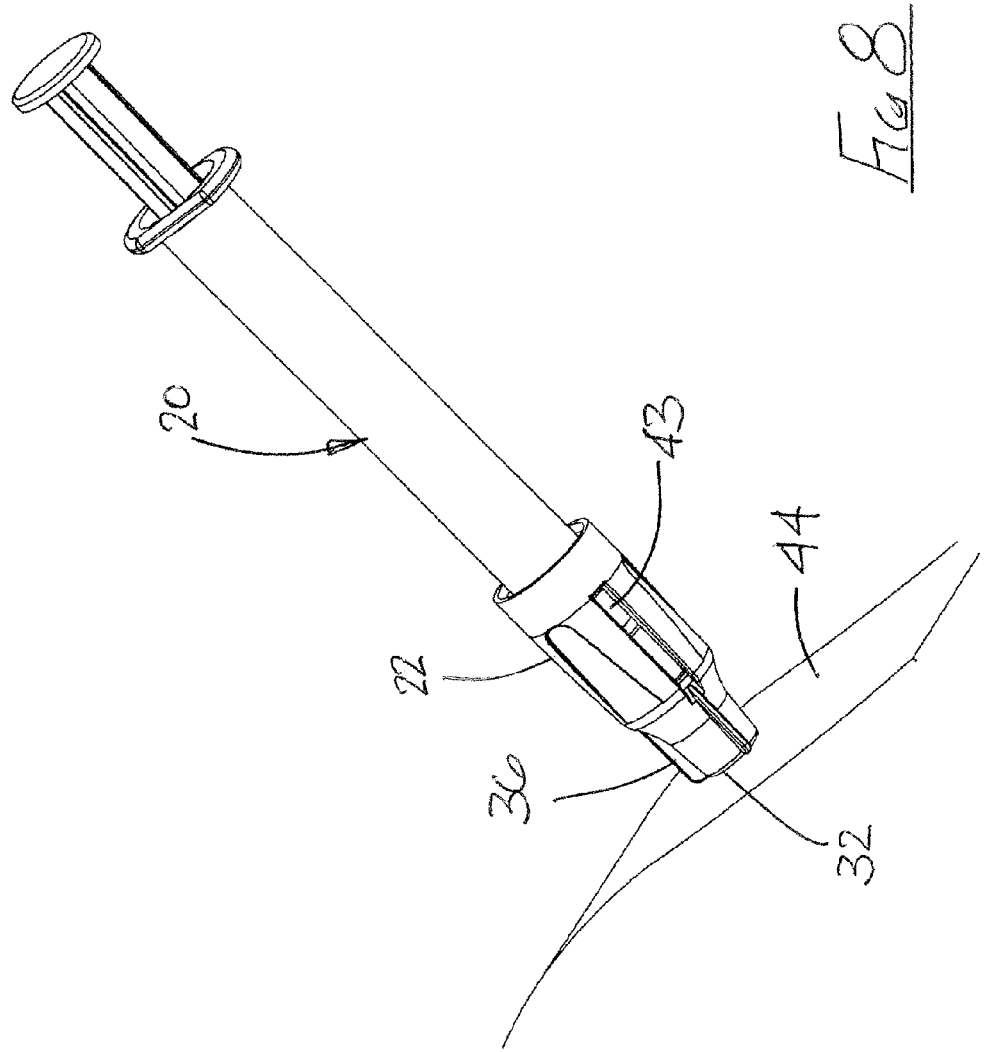

SAFETY NEEDLE PACK

CROSS REFERENCE TO RELATED APPLICATION

The present application is the U.S. national stage application of International Application PCT/GB2007/050622, filed Oct. 11, 2007, which international application was published on Apr. 17, 2008 as International Publication WO 2008/044067. The International Application claims priority of British Patent Application 0620117.2, filed Oct. 11, 2006.

This invention relates to a safety needle pack comprising a safe needle device contained within a housing, for use with a syringe or other injector device.

Though this invention relates to a safety needle pack intended for use in performing an injection by the needle of the safe needle device penetrating a human or animal body, the safe needle device could be used for other medical purposes such as the penetration of a pierceable membrane of an intravenous medication system. In the following all medical uses of the safe needle device will be described simply as the penetration of a body, even though specific embodiments may be intended for other medical uses.

Throughout this specification the terms forward and forwardly used in relation to the safety needle pack, the safe needle device and a syringe for use therewith refer to those ends of the components which are approached to a body when a procedure is to be performed, and the direction towards those ends. Conversely, the terms rearward and rearwardly refer to those ends of the components opposed to the forward ends and the direction away from those forward ends.

Fluids of various kinds may be administered to a human or animal body by means of a hollow needle in conjunction with a source of the required fluid. For example, such a needle may be used in conjunction with a syringe holding a liquid drug which may be contained directly in the syringe barrel or in a cartridge located within the syringe, the needle being used to penetrate the body at the site at which the drug is to be received. Equally, body fluids may be withdrawn by using a hollow needle which is used to penetrate the body until the tip is located at the site from which fluid is to be withdrawn.

A recognised hazard for clinicians and other persons using medical needles for the above described purposes, as well as people who may be exposed to used needles in the course of the disposal of those needles, is the risk of a so-called needle-stick injury—that is to say the accidental penetration of a person's skin by the needle. Prior to the use of the needle to supply a fluid to or to withdraw fluid from a body, this rarely presents much of a problem, though once the needle has been used on a body, there is a very much higher risk of a serious consequence for a person suffering a needle-stick injury. During use of the needle to penetrate the body tissues of a patient, the needle is likely to become contaminated with various organisms; should a person subsequently suffer a needle-stick injury, infection could occur.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

A device which protects a needle tip after use without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, when needle-stick accidents can occur.

There is a significant demand for a passive protection device for use with a needle, and which allows a clinician or perhaps others to use the needle in much the same way as is done with an unprotected needle, but which can be manufactured economically and which provides a high degree of protection against needle-stick injury. In the case of health professionals, this demand is driven by health and safety legislation but in the case of others performing self-injections using a so-called pen injector, the used needles must be disposed of safely with minimum risk to others, even in the event that a sharps container is not immediately available. Further, particularly for self-injections, it is highly preferred that the device operates fully automatically, without intervention by the user, so as wholly to prevent access to the needle tip after use, other than by a determined attempt to override the protection. In this way, protection may be afforded not just to the clinician or other user of the needle, but also to people who could come into a risky situation with used needles, such as waste disposal operators, cleaners, and so on.

It is often advantageous for a safe needle device having a sleeve to shroud a needle to have an intermediate setting where the needle tip is exposed to a small extent, before use. This is to allow aspiration of the syringe, and also to allow the operator to observe the precise point of penetration of a body. When full protection is to be achieved after performing an injection, the sleeve must be moved to a position where the needle is wholly covered, and so to a position further forwardly with respect to the needle than the intermediate setting. If a spring is arranged to provide a force on the sleeve to move it to the final fully-protecting position, that spring will be pre-loaded when the sleeve is in the intermediate setting.

The pre-loading of a spring is not normally an issue if the spring is of metal. However, to reduce manufacturing costs, it is possible to provide a plastics material spring and in that case, the safe needle device must be stored in such a setting that the spring is not pre-loaded, having regard to the memory effect associated with plastics, especially when stored for long periods. Thus, there must be a way in which the sleeve can be moved to the intermediate setting immediately before the safe needle device is to be used to perform an injection, while minimising the risk to an operator in the course of moving the sleeve to that intermediate setting.

The present invention aims at providing a safety needle pack incorporating a safe needle device advantageously in the form of an accessory for a syringe or other injector, which addresses these issues and which is both relatively simple and economic to manufacture, especially on a fully automated production line, and which does not significantly affect a conventional injection procedure when mounted on an injector.

According to this invention, there is provided a safety needle pack comprising a safe needle device contained within a housing, which safe needle device comprises a needle hub supporting a medical needle, a sleeve slidably mounted on the needle hub, a locking mechanism for the sleeve and spring means for urging the sleeve forwardly with respect to the needle hub;

wherein the needle hub is adapted for connection to a syringe and the sleeve is arranged to slide between a protecting position in which the tip of the needle is located inside the sleeve through an intermediate position in which the tip of the needle projects from the sleeve and a retracted position in which a greater length of the needle is exposed, such that, in use, the sleeve is moved to the intermediate position ready for performing an injection and then as the needle is inserted into a patient, the sleeve is moved to the retracted position against the action of the spring means so that on removal of the needle from the patient the spring means moves the sleeve to the protecting position, said locking mechanism then restraining the sleeve in the protecting position;

and wherein the forward end of the housing covers at least the tip of the needle when the safe needle device is located within the housing and the needle hub is exposed through the rearward end of the housing, and connection of a syringe to the hub by rotation of the syringe relative to the hub also turns the device within the housing causing the sleeve to move rearwardly with respect to the housing, setting the sleeve to said intermediate position.

It will be appreciated that with the safety needle pack of this invention, the needle and needle hub do not move forwardly within the housing, in the course of connecting a syringe to the needle hub. Thus, it is relatively easy to perform a twist-locking connection between a syringe and the needle hub, merely by effecting relative rotation between the two. In the course of this, the sleeve is moved rearwardly within the housing, and so with respect to the needle hub, so setting the sleeve to said intermediate position, and also pre-loading the spring means. Conveniently, the needle hub defines one of a Luer slip, or Luer lock socket for mating with a correspondingly-formed Luer slip or Luer lock taper spigot on a syringe, requiring a twisting motion to complete the connection. Alternatively, the needle hub could define an internally-threaded socket for engagement with an externally threaded spigot on the syringe, as with a so-called pen injector.

Rotational driving of the needle hub by the connection of a syringe thereto must also turn the sleeve; thus, there may be co-operating profiles to resist relative rotation between the needle hub and the sleeve, while still permitting relative axial sliding movement.

In order to effect rearward movement of the sleeve as the needle hub is turned by the connection thereto of a syringe, the external surface of the outer sleeve and the inner surface of the housing may have co-operating profiles to move the sleeve rearwardly. For example, a cam profile may be formed within the housing, the sleeve having a cam follower formed on its external surface for engaging the cam profile. A stop may be formed within the housing to limit the rotational movement of the sleeve, when the sleeve has been moved to the intermediate position with respect to the needle hub.

The sleeve may have a rearward portion defining a parallel bore within which the needle hub is received, and a forward portion which tapers inwardly in the forward direction. The locking mechanism may comprise a locking member slidably mounted on the needle hub, the locking member including a locking portion engageable with the sleeve, for example behind a shoulder formed internally within the sleeve in the region of the junction between the rearward and forward portions thereof. In this case, a camming surface may be arranged within the sleeve to turn the locking member from an initial position with respect to the sleeve in the course of the movement of the sleeve to its retracted position, to bring the locking portion into alignment with the shoulder for engagement therewith on subsequent movement of the sleeve to its protecting position.

The locking member may include at least one, but preferably three forwardly-projecting fingers each resiliently deformable inwardly by the inwardly-tapering forward portion of the sleeve, as the sleeve moves rearwardly with respect to the locking member. For this arrangement, the inwardly-tapering forward portion of the sleeve may include a detent partway along the length thereof and which is engageable by a nib on the or each finger on rearward movement of the sleeve as a syringe is connected to the safe needle device, thereby to hold the sleeve in its intermediate position.

A tube preferably extends rearwardly from the closed forward end of the housing and receives the needle, the rearward end of the tube directly engaging the needle hub, or indirectly engaging the hub through the locking member, thereby to limit forward movement of the needle hub.

The locking mechanism may include an indicator, such as a coloured strip, which is visible through a window in the sleeve, the indicator being brought into alignment with the window following the performance of an injection and the sleeve moving forwardly to its protecting position. Such an indicator may serve to show when the safe needle device has been used to perform an injection and that the sleeve has been locked in its protecting position. The indicator will thus show that the needle of the safe needle device has been made safe.

By way of example only, one specific embodiment of safety needle pack arranged in accordance with this invention and intended for use with a syringe, and also a modification of that pack will now be described in detail, reference being made to the accompanying drawings, in which:

FIG. 1 is an isometric view of the safety needle pack, as manufactured and ready for use;

FIG. 2 shows the pack of FIG. 1 with a seal removed and being offered to a syringe;

FIG. 3 shows the pack of FIGS. 1 and 2 but partially cut away for clarity, in the course of being connected to a syringe;

FIG. 4 is similar to FIG. 3 but at the completion of the connection;

FIG. 5 shows the syringe and safe needle device connected together and removed from a housing;

FIGS. 6 and 7 are axial sections through the safety needle pack of FIGS. 4 and 5 respectively, on an enlarged scale;

FIGS. 8 and 9 show a modified form of the safe needle device of FIG. 5 but including an indicator to show when the safety needle has been locked against subsequent use.

Figure 9:
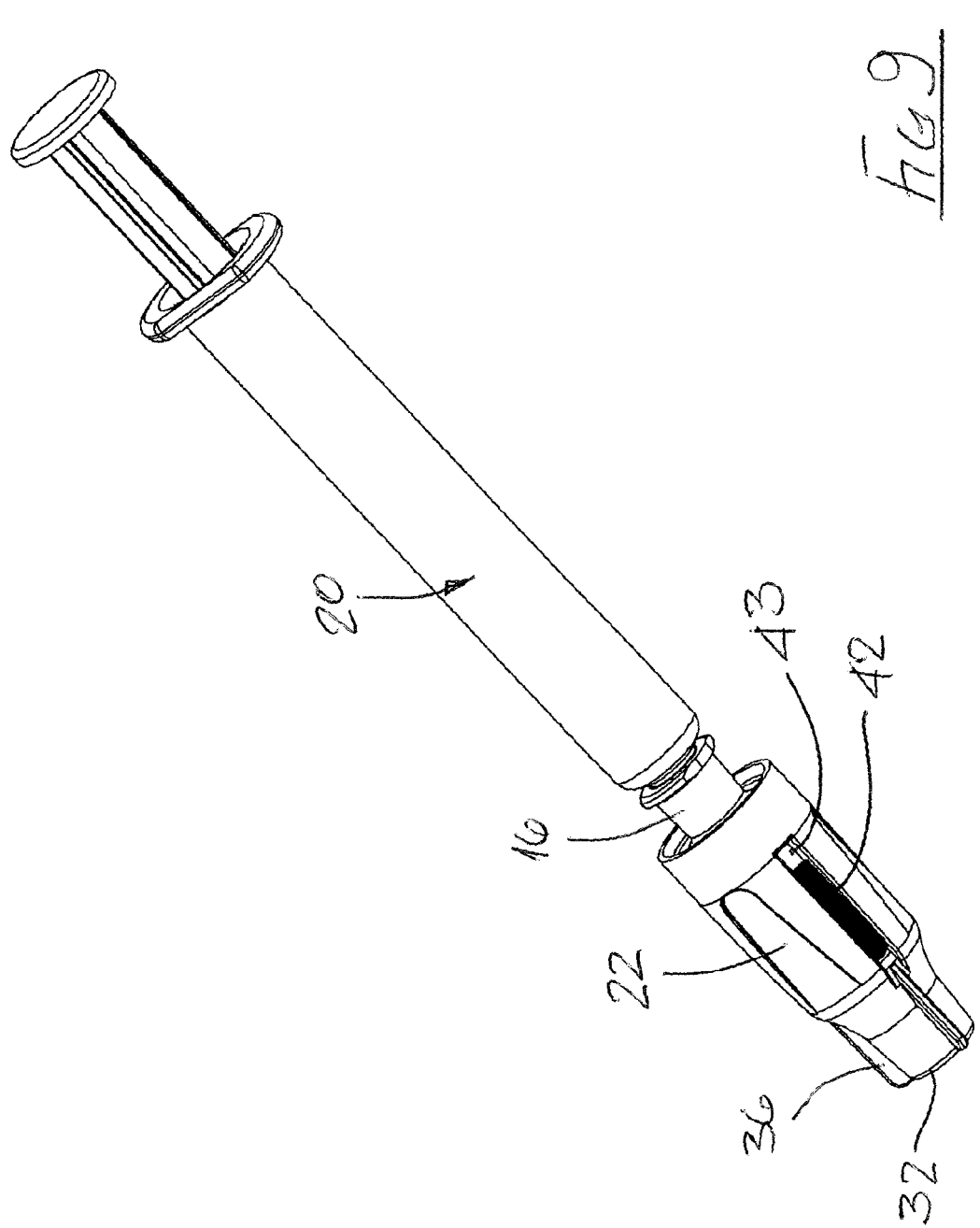

Referring initially to FIG. 1, there is shown a safety needle pack arranged in accordance with this invention and comprising a housing 10 closed at one end 11, the other end 12 being open but sealed by a strippable foil 13. The external surface of the housing 10 has external axially-extending ribs 14, to facilitate handling of the pack.

Contained within the housing 10 is a safe needle device which includes a needle hub 16 supporting a needle 17 to project forwardly from the hub, the hub defining a rearwardly facing socket 18 for receiving a correspondingly profiled spigot 19 on an single-use pre-charged syringe 20. The spigot and socket may take a known form such as a Luer slip profile or could be threaded and so define a Luer lock profile. In either case, the connection is made by rotating the syringe with respect to the needle hub such that the needle hub locks on to the syringe spigot. These profiles form no part of the present invention and so will not be described in further detail here.

The needle hub 16 includes a generally cylindrical formation 21 on which is slidably mounted a protective sleeve 22, interengaging ribs and grooves (not shown) being formed on the hub and sleeve, to prevent relative rotation therebetween. The sleeve has a rearward portion 23 defining a parallel bore which slides on the formation 21 and a forward portion 24 which tapers inwardly, as will be described in further detail below. Three detents 25 are equi-spaced internally around the forward portion, partway between the end thereof.

A locking member 27 has a central part 28 which is slidably carried on the needle hub 16, three equi-spaced fingers 29 projecting forwardly from the central part 28 and each finger 29 having a nib 30 at its forward end. The fingers are resiliently deformable in the radially inward direction, by a force applied to the nibs so flexing those fingers and the junction thereof with the central part 28. As shown in FIGS. 6 and 7, the nibs may locate in the detents 25 and when so positioned, the forward tip 31 of the needle projects slightly beyond the forward end 32 of the sleeve 22. When the nibs are disposed at the junction 33 between the rearward and forward portions 23 and 24 of the protective sleeve, the sleeve fully covers the needle 17. Conversely, when the nibs are adjacent the forward end of the sleeve, the needle projects to its fullest extent, for performing an injection.

Projecting internally within the housing 10 from the closed one end 11 thereof is an internal tube 35, which engages the forward end of the central part 28 of the locking member 27. In turn, the rearward end face of the locking member 27 engages the needle hub 16, so preventing any forward movement of the needle hub and the locking member, when the safe needle device is stored within the housing.

The external surface of the protective sleeve 22 has three equi-spaced ribs 36 extending axially and serving to locate the sleeve within the housing 10. The forward ends 37 of the ribs terminate at the forward end of the protective sleeve and as best seen in FIGS. 3 and 4, each forward end 37 engages a respective cam profile 38 formed internally within the housing 10, adjacent the closed one end 11 thereof. Rotation of the sleeve in the direction of arrow A shown on FIGS. 3 and 4, from a starting point with the forward ends 37 of the ribs at the closed one end 11 of the housing, will drive the sleeve 22 rearwardly as those forward ends 37 ride up the respective cam profiles 38.

Referring again to FIGS. 1 and 2, the safe needle device as manufactured and prepared for storage before subsequent use is located in the housing 10 with the central part 28 of the locking member 27 engaging the tube 35 and the needle hub 16 engaging that central part 28. The needle hub thus cannot move deeper into the housing 10 and the rear face of the needle hub is adjacent the sealing foil 13 closing the other end 12 of the housing. In this setting, the nibs 30 are disposed adjacent the junction 33 (FIGS. 5 and 6) between the rearward and forward portions 24 of the sleeve, and the fingers are essentially unstressed.

A user holds the housing 10 and offers the syringe 20 to the socket 18 of the needle hub 16 (FIG. 2) and as the Luer slip spigot 19 of the syringe is fitted into the needle hub, the syringe is twisted in the direction of arrow A (FIG. 3). The needle hub 16 cannot move deeper into the housing 10 but the rotational movement of the syringe is transferred through the needle hub to the sleeve 22, while the housing is held stationary. This rotational movement slides the sleeve 22 rearwardly, as the forward ends 37 of the ribs 36 on the sleeve ride along the cam profiles 38 formed within the housing 10 (FIGS. 6 and 7). Eventually the position is reached where the nibs 30 engage the detents 25 in the forward portion 24 of the sleeve 22, the ribs 36 at this point engaging a stop 39 (FIG. 4) at the rearward end of the cam profile and so preventing further rotational movement between the sleeve 22 and housing 10.

When the setting of FIG. 4 has been reached, the Luer slip connection is fully engaged and on pulling the syringe 20 away from the housing 10, the safe needle device comes out of the housing, with the tip 31 of the needle exposed beyond the forward end 32 of the sleeve (FIG. 5). The syringe is thus prepared for performing an injection and with the tip of the needle exposed, the medicament within the syringe may be aspirated and also the precise point of entry of the needle tip into a patient can accurately be observed.

On performing the injection, the sleeve 22 is pushed rearwardly by the patient's skin and this action causes relative turning through a few degrees, between the locking member 27 and the sleeve 22, while the nibs 30 move along the internal surface of the forward portion of the sleeve, forwardly of the detents 25. This also resiliently deforms the fingers 29 inwardly, so generating a restorative force tending to push the sleeve 22 forwardly with respect to the locking member 27 and so also the needle hub 16. On removing the needle from a patient, the sleeve 22 moves forwardly under the action of that restorative force until the forward ends of the fingers 29 are returned to the region of the junction between the forward and rearward portions of the sleeve. In view of the rotational movement of the locking member with respect to the sleeve, the forward ends of those fingers drop behind a shoulder 40 formed at the junction such that the fingers thereafter prevent further retracting movement of the sleeve 22 with respect to the needle 17. The needle is thus protected against exposure once more.

The entire assembly of the single-use syringe together with the safe needle device mounted on the forward end of that syringe may now be disposed of in the usual way, for example, in a sharps box.

Referring now to FIGS. 8 and 9, there is shown a modified form of the device described above. Here, a strip 42 of colour is formed along the outer surface of one of the fingers 29 of the locking member 27 and the sleeve 22 is provided with a window 43 in the form of an axial slot in the rearward portion 23 of the sleeve. Prior to performing an injection, the fingers of the locking member 27 are out of rotational alignment with the window 43 and so the strip 42 cannot be seen. As shown in FIG. 8, when performing an injection the sleeve 22 moves fully rearwardly by virtue of the pressure on the skin 44 of a patient, against the action of the restorative spring force provided by the fingers 29 of the locking member. He locking member is turned slightly during the retracting movement of the sleeve, as described above, but the fingers still cannot be seen through the window 43. However, on removing the device from a patient, as shown in FIG. 9, the sleeve moves forwardly under the action of the force provided by the fingers 29, so bringing a finger beneath the window 43. In this setting, with the sleeve locked against retracting movement by the fingers, the coloured strip 42 is visible through the window so showing that the safe needle device has been locked out and preventing the needle being exposed once more.

The invention claimed is:
1. The safety needle pack comprising:
   a safe needle device having a forward end and a rearward end, and comprising a needle hub adapted for connection to a syringe, a medical needle supported by and projecting forwardly from the needle hub and having a sharp tip remote from the hub, a sleeve having an external surface and being slidably mounted on the needle hub, a locking mechanism for the sleeve, and a spring mechanism for biasing the sleeve forwardly with respect to the needle hub;
   wherein:

the sleeve is arranged to slide relative to the hub between a protecting position in which the tip of the needle is located inside the sleeve, through an intermediate position in which the tip of the needle projects from the sleeve, and a retracted position in which a greater length of the needle is exposed, such that in use, relative sliding between the sleeve and the hub sets the sleeve to the intermediate position ready for performing an injection, and then as the needle is inserted into a patient, the sleeve slides over the hub to the retracted position against the action of the spring mechanism, so that on removal of the needle from the patient the spring mechanism moves the sleeve to the protecting position, said locking mechanism then restraining the sleeve in the protecting position; and a housing for removably containing the safe needle device prior to use, said housing having a forward end and an open rearward end and an inner surface therebetween, such that when the safe needle device is located within the housing, the inner surface of the housing is disposed around the outer surface of the sleeve, the forward end of the housing covers at least the tip of the needle and the needle hub is exposed through the rearward end of the housing;

wherein the safe needle device is received rotatably within the housing, and the safe needle device and the housing are configured such that connection of the syringe to the hub by rotation of the syringe turns the safe needle device within the housing to cause said relative sliding of the sleeve and the hub, setting the sleeve to said intermediate position;

the safe needle device comprises a detent arrangement for retaining the sleeve and hub in the intermediate position against the action of the spring mechanism until the sleeve is moved further towards the retracted position, whereby the safe needle device may be removed from the housing with the sleeve and hub held in the intermediate position for performing an injection.

2. The safety needle pack as claimed in claim 1, wherein the needle hub defines one of a luer slip socket, a luer lock socket and an internally threaded socket, for mating with a correspondingly-formed luer slip spigot, a luer lock spigot and an externally threaded boss on the syringe, requiring a twisting motion to complete the connection.

3. The safety needle pack as claimed in claim 1, wherein the external surface of the sleeve and the inner surface of the housing have co-operating profiles to effect said relative sliding of the sleeve and the hub to set the sleeve to the intermediate position when the safe needle device is turned within the housing.

4. The safety needle pack as claimed in claim 3, wherein a cam profile is formed on the inner surface of the housing, and the sleeve has a cam follower formed on the external surface thereof.

5. The safety needle pack as claimed in claim 4, wherein a stop is formed within the housing to limit the rotational movement of the sleeve when the sleeve has been set to said intermediate position with respect to the needle hub.

6. The safety needle pack as claimed in claim 5, wherein said stop is provided at the end of the cam profile furthest from the forward end of the housing.

7. The safety needle pack as claimed in claim 1, wherein the needle hub has a cylindrical outer surface, and the sleeve is slidably mounted on said cylindrical outer surface.

8. The safety needle pack as claimed in claim 7, wherein the sleeve has a rearward portion defining a parallel bore having an inner surface, within which the needle hub is received, and a forward portion that tapers inwardly in the forward direction.

9. The safety needle pack as claimed in claim 7, wherein the inner surface of the sleeve and the outer surface of the needle hub are configured to prevent relative rotation between the needle hub and the sleeve.

10. The safety needle pack as claimed in claim 1, wherein the locking mechanism comprises a locking member that is slidably and rotatably mounted on the needle hub, the locking member including a locking portion that is engageable with the sleeve.

11. The safety needle pack as claimed in claim 10, wherein the needle hub has a cylindrical outer surface, and the sleeve has a rearward portion defining a parallel bore having an inner surface, within which the needle hub is received, a forward portion that tapers inwardly in the forward direction, and a junction formed in the inner surface of the sleeve between the rearward and forward portion of the sleeve, and a shoulder formed in the inner surface of the sleeve in the region of said junction; the locking portion of the locking member being engageable behind said shoulder.

12. The safety needle pack as claimed in claim 11, wherein the locking member is turned from an initial position with respect to the sleeve in the course of the movement of the sleeve from the intermediate position to the retracted position, to bring the locking portion into alignment with said shoulder.

13. The safety needle pack as claimed in claim 10, wherein rearwards sliding movement of the locking member on the hub is limited by engagement of the locking member with the hub, and the locking member includes a forwardly-projecting finger that is resiliently deformable inwardly by the inwardly-tapering forward portion of the sleeve as the sleeve moves rearwardly on the hub to the retracted position.

14. The safety needle pack as claimed in claim 13, wherein the detent arrangement comprises a detent partway along the length of the inwardly-tapering forward portion of the sleeve, and a nib on said forwardly-projecting finger, wherein the detent is engageable by the nib on relative sliding of the hub and the sleeve to the intermediate position as a syringe is connected to the safe needle device, thereby to hold the sleeve relative to the hub in said intermediate position.

15. The safety needle pack as claimed in claim 1, wherein the forward end of the housing is closed and receives the forward end of the safe needle device, the rearward end of the housing being open and the needle hub being exposed through said rearward end.

16. The safety needle pack as claimed in claim 15, wherein a tube extends rearwardly from the closed forward end of the housing and receives the needle, the rearward end of the tube directly or indirectly engaging the needle hub to limit forward movement of the needle hub.

17. The safety needle pack as claimed in claim 1, wherein a tube extends rearwardly from the closed forward end of the housing, terminating in a rear end, and receives the needle, the rearward end of the tube engaging the locking member and the locking member engaging the needle hub, thereby to limit forward movement of the needle hub within the housing.

18. The safety needle pack as claimed in claim 1, wherein the locking mechanism includes an indicator and the sleeve has a window through which said indicator is visible, the indicator being brought into alignment with the window following the performance of an injection and the sleeve moving forwardly to its protecting position.

19. The safety needle pack as claimed in claim 1, wherein the rearward end of the housing is sealed before use by a strippable sealing member.

20. The safety needle pack comprising:
- a safe needle device and a housing removably containing the safe needle device; said safe needle device having a forward end and a rearward end, and comprising a needle hub, a medical needle supported by the needle hub and having a tip, and a sleeve having an external surface and being slidably mounted on the needle hub to slide between a forward protecting position in which the tip of the needle is located inside the sleeve, through an intermediate position in which the tip of the needle projects from the sleeve, and a rearward retracted position in which a greater length of the needle is exposed, a spring mechanism arranged for biasing the sleeve towards said protecting position, and a locking mechanism arranged for restraining the sleeve in said protecting position;
  - wherein the housing has a forward end, a rearward end and an inner surface therebetween, and is configured to receive the safe needle device such that when the safe needle device is located within the housing, the forward end covers at least the tip of the needle, the needle hub is exposed through the rearward end of the housing, the inner surface of the housing is disposed around the external surface of the sleeve, and the safe needle device can rotate within the housing; and wherein said hub is adapted for connection to a syringe by rotation the syringe relative to the hub, whereby connection of the syringe to the needle hub rotationally drives the hub within the housing;
  - first co-operating profiles provided on the needle hub and the sleeve to resist relative rotation between the hub and the sleeve when connecting the syringe to the hub so that rotational driving of the hub also turns the sleeve; and
  - second co-operating profiles provided on the housing and the safe needle device to move the sleeve to its intermediate position when the hub is rotationally driven within the housing.

21. The safety needle pack as claimed in claim 20 wherein said first co-operating profiles include a detent arrangement for holding the sleeve in said intermediate position when moved there by connection of a syringe to the hub.

22. The safety needle pack as claimed in claim 20, wherein said second co-operating co-operating profiles comprise a cam profile that is formed on the inner surface of the housing and a cam follower formed on the external surface of the sleeve.

23. The safety needle pack as claimed in claim 22, wherein a stop is formed within the housing to limit the rotational movement of the sleeve when the sleeve has been moved to said intermediate position with respect to the needle hub.

24. The safety needle pack as claimed in claim 23, wherein said stop is provided at the end of the cam profile furthest from the forward end of the housing.

\* \* \* \* \*